United States Patent [19]

Kirschke

[11] 3,978,716
[45] Sept. 7, 1976

[54] METHOD AND APPARATUS FOR DETERMINING INTERNAL EROSION OF STORAGE TANKS AND REPAIR

[76] Inventor: John A. Kirschke, P.O. Box 125, Boerne, Tex. 78006

[22] Filed: Oct. 1, 1975

[21] Appl. No.: 618,440

[52] U.S. Cl. ................................................. 73/86
[51] Int. Cl.² ........................................... G01N 17/00
[58] Field of Search ............... 73/86, 151, 104, 105; 425/11, 12, 13, 175; 264/36

[56] References Cited
UNITED STATES PATENTS

| | | | |
|---|---|---|---|
| 1,953,452 | 4/1934 | Wertz .................................... | 264/36 |
| 3,046,601 | 7/1962 | Hubbert et al ......................... | 73/151 |
| 3,049,752 | 8/1962 | Jordal et al ........................... | 73/151 |

*Primary Examiner*—Richard C. Queisser
*Assistant Examiner*—Anthony V. Ciarlante
*Attorney, Agent, or Firm*—Willard J. Hodges, Jr.

[57] ABSTRACT

A method and apparatus for accurately determining the depth and extent of erosion in underground gasoline storage tanks at service stations. The apparatus provides for cleaning the interior of the tank adjacent the filler pipe, casting a duplicate of the eroded area by means of a casting cup and injector depositing molding materials, and removing the negative of the eroded area. The equipment comprises a brush and extension handle, a casting cup has a cylindrical body with a rectangular opening in the wall for removing solidified casting. The injector includes an operating rod, a cylinder, a piston, and a dispensing valve. The dispenser may be used for injecting a variety of fluids into the eroded area for dispersing inhibitors, injecting molding materials, and in the repair steps after the tank has been emptied and the eroded area cleaned.

8 Claims, 13 Drawing Figures

METHOD AND APPARATUS FOR DETERMINING INTERNAL EROSION OF STORAGE TANKS AND REPAIR

BACKGROUND OF THE INVENTION

1. Field of the Invention

This invention pertains to casting tools and the techniques for forming an exact replica of an eroded area in an underground gasoline storage tank and repair of the eroded area.

2. Description of Prior Art

A wide variety of approaches have been attempted to investigate this erosion problem. One of the approaches has been sonic graphing of eroded areas, inspection by closed circuit TV cameras. Dentists employ related techniques in producing mouth impressions of damaged or missing teeth. A known, related method for determining wear or erosion in the mechanical fields pertains to the determination of defects in a spur gear employing a casting procedure, such as U.S. Patent to Sawyer, No. 2,601,703, entitled "Method for Testing Surface Defects."

SUMMARY OF THE INVENTION

A common condition exists in underground gasoline storage tanks is highly eroded area in the bottom of the tank just below the filler pipe. The causes are attributed variously to repeated contact with the area by the measuring stick, promoting rusting and erosion due to electrolysis varying with the Ph of the soil. The repeated use of the measuring stick disperses sediments, tends to remove erosion and polishes the area accelerating further erosion.

An object of this invention was to determine and accurately measure the extent of erosion, to ascertain the necessity for repair or replacement.

Another object was to provide suitable tools for casting the eroded area compatible with casting under adverse conditions in underground tanks containing a motor fuel product.

Another object was to design tools capable of casting the eroded area and determining the extent of the erosion and repair the area if required.

In accomplishing the foregoing objectives a brush is used to relatively clean the area. The casting cup is placed over the exposed area and a heavy grade gear oil is injected into the cup to remove casting inhibitors such as alcohol blended with the hydrocarbons in the product. A cylindrical cup of maximum diameter to pass through the filler pipe is used. The cup is sealed to the bottom of the tank employing caulking compound such as caulking strips or other yieldable substances. The cylindrical injector comprises a drive rod, a piston, and a cylinder having a dispensing valve. The procedures employed generally comprise employing the injector to place gear oil in the molding cup positioned in the tank. The gear oil displaces casting inhibitors collecting in the fluid sediment in the tank. The gypsum casting materials in combination with a fluid is injected into the eroded area. Negative casting is formed below the surface of the product in the tank in approximately 15 minutes. The negative casting is removed and a positive casting produced reproducing the eroded area of the tank. If it is necessary to repair the tank, the tank is evacuated and thoroughly cleaned. The same injector or an injector of a larger capacity can repair the eroded area after a thorough cleaning of the area with phosphoric acid or other suitable cleaners. Epoxy or other durable plastic materials may be injected into the eroded area effecting a repair.

BRIEF DESCRIPTION OF THE DRAWINGS

For a detailed description of the invention reference is made to the attached drawings wherein identical reference characters refer to identical or equivalent components throughout the various views and the detailed description.

DESCRIPTION OF THE PREFERRED EMBODIMENT

Figure 1:
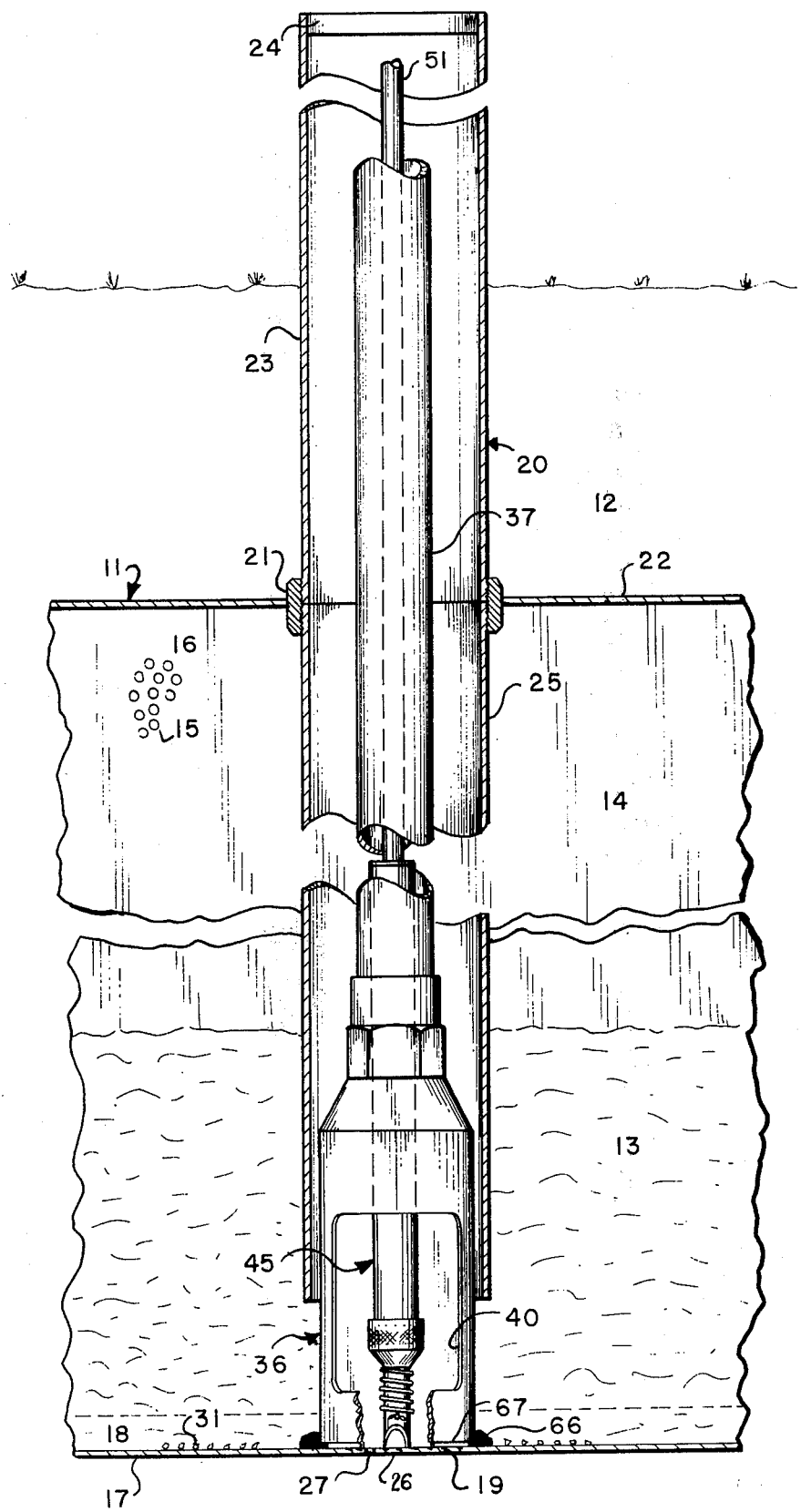
FIG. 1 is a plan view partially fragmented and sectionalized of the tool in combination placed in an underground gasoline storage tank simulating injection of the casting materials.
Figure 5:
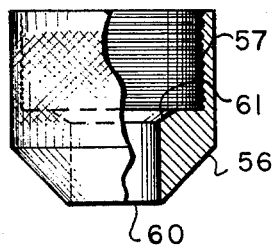
FIG. 5 is a fragmented view of the dispensing valve body.
Figure 6:
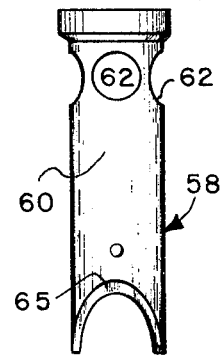
FIG. 6 is a fragmented view of the dispensing nozzle.
Figure 7:
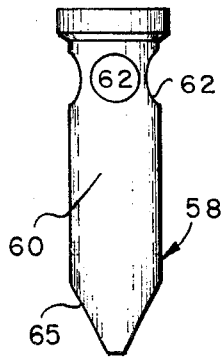
FIG. 7 is a fragmented view of the dispensing nozzle of FIG. 6 rotated 90°.

For a detailed description of the design of the tools employed in association with the method your attention is invited to FIGS. 1–7. For an illustration of the product produced by the tools and the resulting method your attention is invited to FIGS. 8–13.

The tools and the method of this invention are designed for employing in a gasoline storage tank 11 embedded in the soil 12. The unusual environment impose particularly demands in the fact that the tank 11 contains a product 13. The upper part of the tank 11 usually contains a mixture of gas and air 14. Condensed water vapor 15 collects on the interior walls 16 of the tank 11. The bottom 17 of tank 11 usually contains a strata of collected fluid sediments 18 and scale and erosion 19 on the bottom 17 of tank 11 just below filler pipe 20. Filler pipe 20 normally comprises a collar 21 mounted in the top 22 of tank 11. Upper filler pipe 23 is attached to collar 21 having a cap or cover 24. Projecting into tank 11 is the lower filler pipe 25 which extends to a point closely adjacent the bottom 17 of tank 11. In this general area is located the scale and eroded area 19 which creates the problems this invention is designed to solve. This specific eroded area 26 can progress in tank 11 under certain soil 12 conditions to such an extent as to produce a perforation 27 of tank 11. This permits a leakage of the product 13 or might permit water to flow into the tank 11. The presence of water in the fluid sediment 18 is usually a collection of condensed water vapor 15 collected from the interior wall 16 of tank 11.

For a description of the specific tools performing the methods of this invention attention is invited particularly to FIGs. 1–7. Tools for practicing the method and producing the desired results are illustrated in FIGS. 1–7 comprising a brush 30 for removing solid sediments 31 from the eroded area 26. The tools are constructed of various diameters of 2, 3 and 4 inches. The particular tool selected is determined by the diameter of the filler pipe 20. The largest diameter which will pass through the filler pipe 20 is preferably used.

Figure 2:
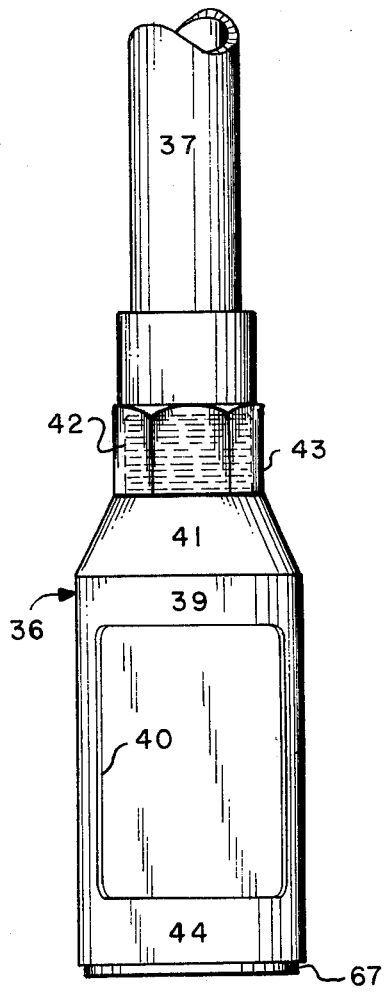
FIG. 2 is a plan view of the casting cup and the extension shaft.
Figure 3:
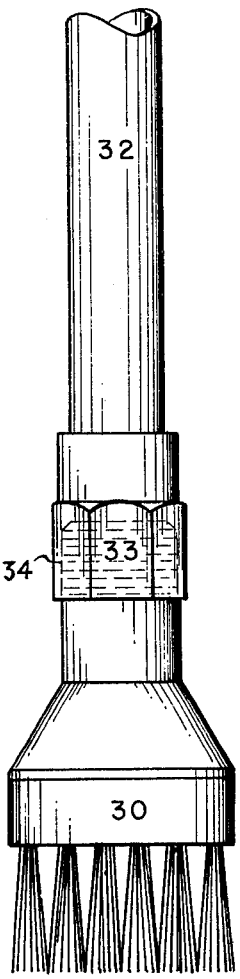
FIG. 3 is a plan view of the cleaning brush and the extension handle
Figure 4:
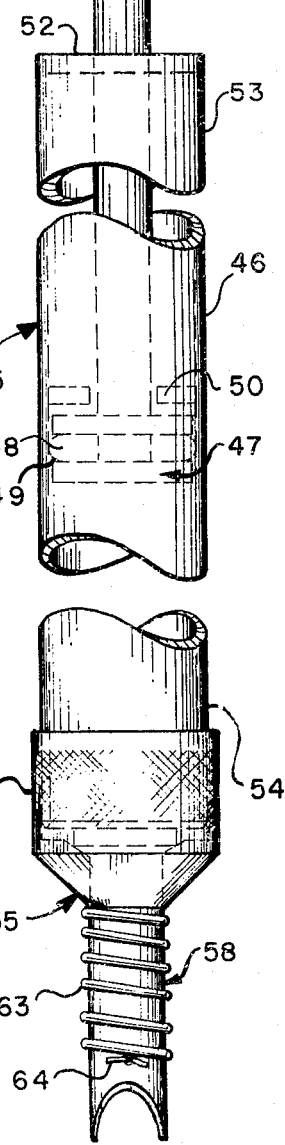
FIG. 4 is a detailed view partially fragmented illustrating the injector.
Figure 8:
FIG. 8 is an illustration of the eroded area of the bottom of the tank.

For a description of the construction of the specialized tools reference is particularly made to FIGS. 1–7. The brush 30 is used to remove the solid sediments 31 in the vicinity of the eroded area 26 prior to initiating the further procedures of this method. Brush 30 is mounted on an extension handle 32 which was constructed from a section of plastic pipe having an inside diameter of 1¼ inches. Extension handle 32 included an extension handle collar 33 at one end having a threaded inside diameter of 1½ inches. The threaded arm 34 of brush 30 was screwably attached to extension handle collar 33. The brush 30 might be of various configurations and design; however, the preferred embodiment was constructed in the general configuration as illustrated in FIG. 3. The characteristic of the brush should be rather sturdy. In the preferred embodiment a coarse fiber bristle brush was employed. The extension handle 32 was constructed of sections of PVC pipe 4' in length. If an extension handle 32 of greater length is required sections of pipe may be screwably connected together in an integral structure.

For a description of the construction of the casting cap 36 reference is particularly made to FIG. 2. An extension shaft 37 constructed of plastic PVC pipe is employed. The pipe in this instance has an inside diameter of 1½ inches. The casting cap 36 was constructed from a block of aluminum alloy using conventional machining processes. The cup 36, however, might be constructed by casting, extrusion, or even by injection molding of metal or plastic. As previously stated the casting cups 36 are constructed with three sizes having a diameter of 2, 3 and 4 inches. The 3 inches model of the casting cup was constructed with 3 inches inside diameter and a 3¼ inches outside diameter. Cylindrical body 39 was 5 inches long having a rectangular aperture 40 in one side wall 3¾ inches by 3½ inches. The dimensions of this rectangular aperture 40 is somewhat optional in that it is employed only to remove castings which will be hereinafter described. Casting cup 36 is constructed with a sloping collar 41 approximately 2 inches long of the general configuration illustrated in FIG. 3 including a threaded connector 42 which is screwably connected to the extension shaft collar 43. Casting cup 36 includes a casting collar 44 at the end of the cylindrical body opposite the sloping collar. The casting collar 44 has a height of 1 inch. These dimensions might vary in various designs of the casting cup.

For a description of the construction of the injector 45 attention is invited to FIGS. 1, 4–7. In the preferred embodiment injector 45 included an injector cylinder 46 17 inches long having an inside diameter of 1 inch. Movably mounted internal of the injector cylinder 46 was injector cylinder piston 47 having a diameter of 1 inch and including an O-ring 48 mounted in a piston groove 49 sealing piston 47 in relation to the injector cylinder 46. Approximately in the center of injector cylinder 46 was constructed a rod stop 50 through which operating rod 51 projects. The rod stop 50 in conjunction with injector cylinder piston 47 and rod guide 52 limit the movement of injector cylinder piston 47 regulating the capacity of the injector. In the preferred embodiment the positioning of rod guide 52 relative injector cylinder piston 47 limit the movement of the rod guide 52 to the top 53 of the cylinder and injector cylinder piston 47 to the bottom 54 of the cylinder. A dispensing valve 55 was threadably secured to the bottom 54 of the cylinder. The construction of the valve is illustrated in FIGS. 4–7. The valve includes a valve body 56 having dispensing nozzle threads 57 for attaching the device to injector cylinder 46. Movably mounted in dispensing valve body 56 is the dispensing nozzle 58 constructed with dispensing nozzle throat 60 projecting along its axis approximately for its entire length. At the upper end of dispensing valve 55 was constructed a valve seat 61. Just below this valve seat 61 was constructed a multiplicity of feed apertures 62 projecting into dispensing nozzle throat 60. Mounted external of dispensing nozle 58 is a closing spring 63 placed under compression load around dispensing nozzle 58 and secured in position by securing pin 64. To facilitate the materials being discharged from the dispensing nozzle 58 release slots 65 were formed in each side of dispensing nozzle 58.

The foregoing substantially describes the specialized equipment design. The materials utilized in association with the equipment will be further described in the description of the procedures of the process.

DESCRIPTION OF THE METHOD AND OPERATION

The first step of the casting procedure would be to place brush 30 in the tank 11 through filler pipe 20 and rotate the brush 30 to remove any solid sediments 31 from eroded area 26. The next step is to attach a rope-like segment of caulking compound 66, such as "Finger-Tite Caulking Strips" distributed by Maclanburg-Duncan Co. of Oklahoma City, Okla., around the bottom edge 67 of casting cup 36. The next step is to place the casting cup 36 in the filler pipe 20 pressing down slightly to seal the casting collar 44 against the bottom of the tank 17 over the eroded area 26. Next we fill injector 45 with 90 weight gear oil. Injector 45 is positioned through the extension shaft 37 and downward pressure on injector 45 permits the gear oil to flow into and fill the area of casting collar 44. This procedure displaces certain casting inhibitors which are present in the fluid sediments 18 in the bottom of tank 17. Gasoline or motor fuels are generally referred to in the industry as the product and include various additives. Among the additives can be alcohol which is an inhibitor to solidifying of the casting materials employed in the process of this invention. The injection of the gear oil displaces the inhibitors from the area of casting collar 44. The next step of the procedure is to fill the injector with a charge of casting materials. Among the satisfactory casting materials used in the preferred procedure was compound containing gypsum sold under the trade name of "Denstone" by Modern Materials of St. Louis, Mo. Another satisfactory material which may be acquired in most dental supply houses is "Caststone." A charge for the injector is a mixture of 50 percent and 50 percent of the powdered Denstone or Caststone. Under adverse casting conditions where the tank 11 has shifted or there is a perforation 27 of tank 11, a thicker mixture, such as one part water to 4 parts powder may be employed. After filling the injector 45 with the charge, the next step is to inject the casting materials into casting cup 36 filling the area internal of the casting collar 44. The next step is to allow the casting materials to remain in position for approximately 15 minutes to solify. Caststone and Denstone will solidify in approximately 10 minutes; however, under varying temperature conditions it has been discovered that a setting time of 15 minutes in this procedure is normally satisfactory under any conditions. Next, remove the casting cup 36 lifting the negative casting 68 from the storage tank 11. Next, remove the negative casting 68 from the casting cup 36. This may be accomplished by bumping the casting with the hand at the bottom edge 67 of the casting cup 36 and removing the casting through the rectangular aperture 40.

Figure 9:
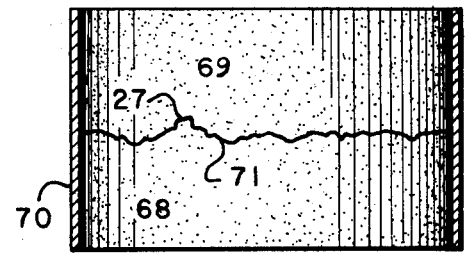
FIG. 9 is a sectional view of the positive casting being produced from the negative casting.
Figure 10:
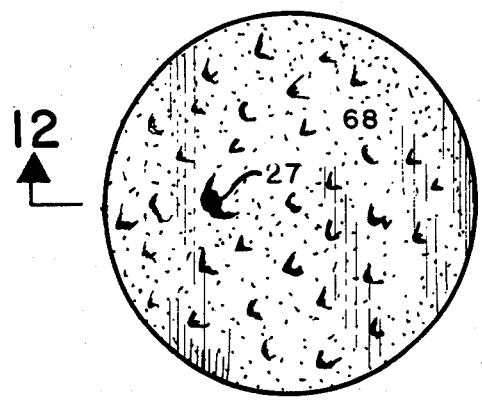
FIG. 10 is a negative casting.
Figure 11:
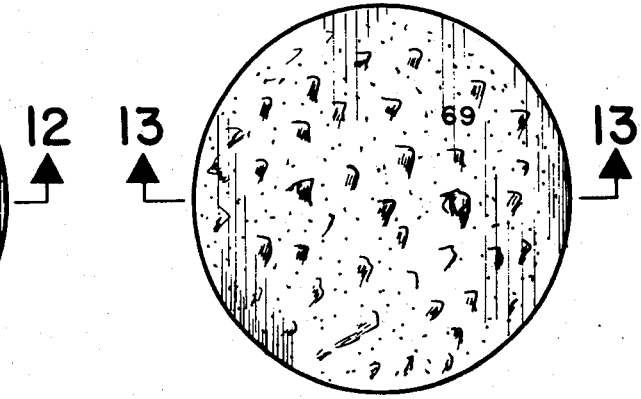
FIG. 11 is a positive casting.
Figure 12:
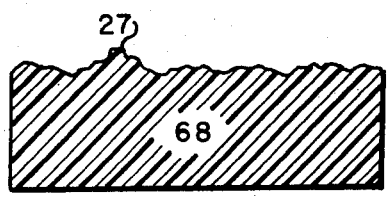
FIG. 12 is a sectional view of the negative casting taken substantially on line 12—12 of FIG. 10.
Figure 13:
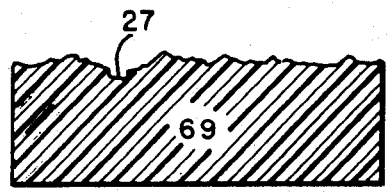
FIG. 13 is a sectional view of the positive casting taken substantially on line 13—13 of FIG. 11 looking in the direction of the arrows.

If desired, the following procedures may be followed to produce a positive casting 69. Coat the surface of negative casting 68 with release assisting coating, such as "Liquid Foil 71" used by Dentists. Next, place a collar of masking tape 70 around negative casting 68 substantially as illustrated in FIG. 9. Next, prepare a mixture of the Denstone or Caststone 50—50 mixture with water or a more fluid mixture and pour a positive cast 69 into the void above negative casting 68. Permit the materials to set for approximately 15 minutes and remove the tape 70 separating the negative casting 68 and the positive casting 69. Next, break the positive and negative castings apart by applying pressure to the castings. This procedure results in an exact reproduction of eroded area 26 in the bottom of the tank 17.

To repair the eroded area 26 in instances where there is perforation 27 in the bottom 17 of the tank 11, the tank would normally be required to be completely evacuated of any fluid and the interior of the tank particularly in the eroded area 26 thoroughly cleaned. This cleaning might be accomplished by various cleaning methods such as buffing or cleaning the area with phosphoric acid. After the area is thoroughly cleaned and dry, a method of repair would be to fill the injector 45 or an injector having a larger capacity than the one described in the foregoing description with epoxy or other suitable repair materials. Materials may be positioned through the filler pipe 20 and placed over the eroded area 26 and dispensed. When the epoxy or other durable fluid solidifying repair materials are placed in position they solidify, closing the perforation 27 and repairing the eroded area 26.

Having described in detail the equipment and procedures for practicing this invention including the detailed steps of the process; what is desired to be claimed is all methods and tools not departing from the scope of this invention as defined in the appended claims.

I claim:

1. A tool combination for performing a method measuring erosion in a storage tank comprising:
   a. a casting cup adapted to form the casting in the gasoline storage tank, said casting cup comprising:
      1. an elongated, cylindrical body having an outer wall,
      2. an aperture formed in the wall of said cylindrical body, and
      3. a cylindrical casting collar extending from said aperture to the bottom edge of said casting cup,
   b. an extension shaft having an axial inside diameter attached to said casting cup,
   c. an injector projecting axially through said extension shaft into the interior of said casting cup, and
   d. means for dispensing casting materials from said injector into said casting cup.

2. The invention of claim 1 wherein said aperture formed in the wall of said cylindrical body is a rectangular aperture.

3. The invention of claim 1 wherein said injector further comprises:
   a. elongated injector cylinder,
   b. a piston movably positioned in said elongated cylinder,
   c. an elongated operating rod attached to said piston and projecting from the top of said injector cylinder, and
   d. a pressure activated, dispensing valve secured to the bottom of said injector cylinder.

4. The invention of claim 3 wherein said dispensing valve further comprises:
   a. a dispensing valve body,
   b. a dispensing valve seat internal of said dispensing valve body,
   c. a dispensing valve nozzle extending from said valve body terminating at a bottom end,
   d. a dispensing nozzle throat internal of said dispensing nozzle, and
   e. a closing spring urging said valve seat to a closed position, said valve seat opening when pressure is applied to the bottom end of said dispensing nozzle.

5. A method for determining the internal erosion of a storage tank comprising the steps of:
   a. placing a casting cup through the filler pipe,
   b. sealing the cup against the interior wall of said storage tank,
   c. inserting an injector filled with heavy oil into the casting cup,
   d. injecting the said heavy oil into the casting cup displacing casting inhibitors from the casting collar,
   e. inserting an injector into the casting cup filled with a casting mixture,
   f. injecting the casting mixture into the casting cup,
   g. permitting the casting cup to remain in position until the casting compound solidifies,
   h. removing the casting cup and the solidified negative casting from the storage tank, and
   i. inspecting the solidified casting to observe the extent of erosion in the casting area.

6. The invention of claim 5 including the following preliminary step:
   a. brushing the interior wall of the storage tank adjacent the end of the filler pipe to remove loose sediments.

7. The invention of claim 5 including the following additional steps:
   a. removing the solidified negative casting from the casting cup,
   b. applying a release assisting coating to the said negative casting, and
   c. casting a positive casting in contact with said negative casting.

8. The invention of claim 5 including the following repair steps:
   a. cleaning the interior of said tank in the eroded area adjacent the end of the filler pipe,
   b. injecting a repair material into the eroded area, and
   c. sealing the eroded area.

* * * * *